(12) United States Patent
Reddy et al.

(10) Patent No.: US 7,022,854 B2
(45) Date of Patent: Apr. 4, 2006

(54) FORMS OF DUTASTERIDE AND METHODS FOR PREPARATION THEREOF

(75) Inventors: Manne Satyanarayana Reddy, Hyderabad (IN); Chakilam Nagaraju, Secunderabad (IN); Gudipati Srinivasulu, Hyderabad (IN); Mandava Venkata Naga Brahmeshwar Rao, Hyderabad (IN); Bojja Ramachandra Reddy, Hyderabad (IN); Singamsetty Radhakrishna, Hyderabad (IN)

(73) Assignees: Dr. Reddy's Laboratories, Limited, Hyderabad (IN); Dr. Reddy's Laboratories, Inc., Bridgewater, NJ (US)

( * ) Notice: Subject to any disclaimer, the term of this patent is extended or adjusted under 35 U.S.C. 154(b) by 222 days.

(21) Appl. No.: 10/622,098

(22) Filed: Jul. 17, 2003

(65) Prior Publication Data
US 2004/0077673 A1 Apr. 22, 2004

(30) Foreign Application Priority Data
Jul. 17, 2002 (IN) .................................. 534/MAS/2002

(51) Int. Cl.
*C07D 221/18* (2006.01)
*C07D 221/02* (2006.01)

(52) U.S. Cl. ............................. 546/77; 546/61; 514/284
(58) Field of Classification Search .................. 546/77, 546/61; 514/284
See application file for complete search history.

(56) References Cited

U.S. PATENT DOCUMENTS 5,565,467 A * 10/1996 Batchelor et al. ........... 514/284

* cited by examiner

*Primary Examiner*—Charanjit S. Aulakh

(57) ABSTRACT

A crystalline Form II of 17β-N-[2,5-bis (trifluoromethyl) phenyl]carbamoyl-4-aza-5-α-androst-1-en-3-one (dutasteride) is provided. The preferred crystalline Form II of dutasteride has an X-ray powder diffraction pattern, expressed in terms of d-spacing (in °A), with peaks at about 13.42, 6.96, 6.13, 5.27, 4.77, 4.70, 4.58, 4.46 and 3.82. A process for preparation of a crystalline Form II of dutasteride is also provided and includes dissolving a crude form of dutasteride in an alcoholic solvent having from 1 to 5 carbon atoms; removing the alcoholic solvent to obtain a residue; adding an ester solvent to the residue; and filtering the resulting separated solids. The processes of the invention are believed to be simple, eco-friendly, and commercially viable.

16 Claims, 5 Drawing Sheets

FORMS OF DUTASTERIDE AND METHODS FOR PREPARATION THEREOF

FIELD OF THE INVENTION

The present invention relates to amorphous and crystalline forms of dutasteride and the processes for preparing them.

BACKGROUND OF THE INVENTION

Dutasteride, which is chemically known as 17β-N-[2,5-bis (Trifluoromethyl) phenyl]carbamoyl-4-aza-5-α-androst-1-en-3-one (formula (I)),

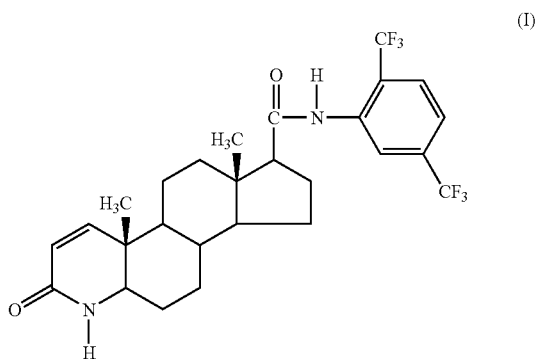

is useful in the treatment of androgen responsive and mediated diseases.

U.S. Pat. No. 5,565,467, incorporated herein by reference, describes and claims dutasteride and related compounds, the pharmaceutical formulations containing them, and their use in the treatment of androgen and mediated diseases. The '467 patent discloses a process for preparation of dutasteride, which includes dehydrogenation of 17β-N-(2, 5-bis (trifluoromethyl)phenyl)carbamoyl-4-aza-5α-androstane-3-one in the presence of catalysts 2,3-dichloro-5, 6-dicyano-1, 4-benzoquinone (DDQ) and bis (trimethylsilyl)trifluoroacetamide in dioxane as solvent and the resultant solid is crystallized from a mixture of ethyl acetate—heptane at a ratio of 1:1 v/v. International Application No. WO 9507927 discloses a process for isolation of pure dutasteride by crystallization of crude dutasteride in methanol and acetonitrile. Nevertheless, new forms of dutasteride and new methods of making dutasteride are desirable.

SUMMARY OF THE INVENTION

In accordance with one aspect, the invention provides a crystalline Form II of 17β-N-[2,5-bis(trifluoromethyl) phenyl]carbamoyl-4-aza-5-α-androst-1-en-3-one (dutasteride). Preferably, the crystalline Form II of dutasteride has an X-ray powder diffraction pattern, expressed in terms of d-spacing (in ° A), that includes peaks at about 13.42, 6.96, 6.13, 5.27, 4.77, 4.70, 4.58, 4.46 and 3.82.

In accordance with another aspect, the invention provides a process for preparation of a crystalline Form II of dutasteride that includes dissolving a crude form of dutasteride in an alcoholic solvent having from 1 to 5 carbon atoms; removing the alcoholic solvent to obtain a residue; adding an ester solvent to the residue; and filtering the resulting separated solids. The processes of the invention are believed to be simple, eco-friendly, and commercially viable.

In accordance with yet another aspect, the invention provides a process for preparation of crystalline Form I of dutasteride that includes dissolving a crude form of dutasteride in a halogenated hydrocarbon solvent; removing the solvent to obtain a residue; adding an aliphatic hydrocarbon solvent of low molecular to the residue thereby obtaining a separated solid; and filtering the separated solid that is the crystalline Form I of dutasteride.

In accordance with yet another aspect, the invention provides an amorphous form of dutasteride. A process for preparation of the amorphous form of dutasteride is also provided and includes dissolving a crude form of dutasteride in an alcoholic solvents having from 1 to 5 carbon atoms; removing the alcoholic solvent to obtain a solid residue; and isolating said solid residue to afford the amorphous form of dutasteride.

DETAILED DESCRIPTION OF THE INVENTION

Polymorphism can be defined as the ability of the same chemical substance to exist in different crystalline structures. The different structures are referred to as polymorphs, polymorphic modifications or forms. The present invention provides crystalline Form I and Form II of dutasteride and processes for their preparation. The crystalline Form I and Form II of dutasteride are characterized by X-ray powder diffraction, which are obtained using Bruker Axe, DS Advance Powder X-ray Diffractometer with Cu K alpha-1 Radiation source.

In one embodiment, the process for preparation of crystalline Form I of dutasteride includes
(i) dissolving a crude form of dutasteride in a halogenated hydrocarbon solvent, preferably, dichloromethane;
(ii) distilling the solvent from the reaction solution;
(iii) adding a low molecular aliphatic hydrocarbon solvent, such as cyclohexane to the resultant residue obtained in step (ii);
(iv) filtering the crystallized solid accompanied by drying the compound in conventional methods to afford the crystalline Form I of dutasteride.

Figure 1:
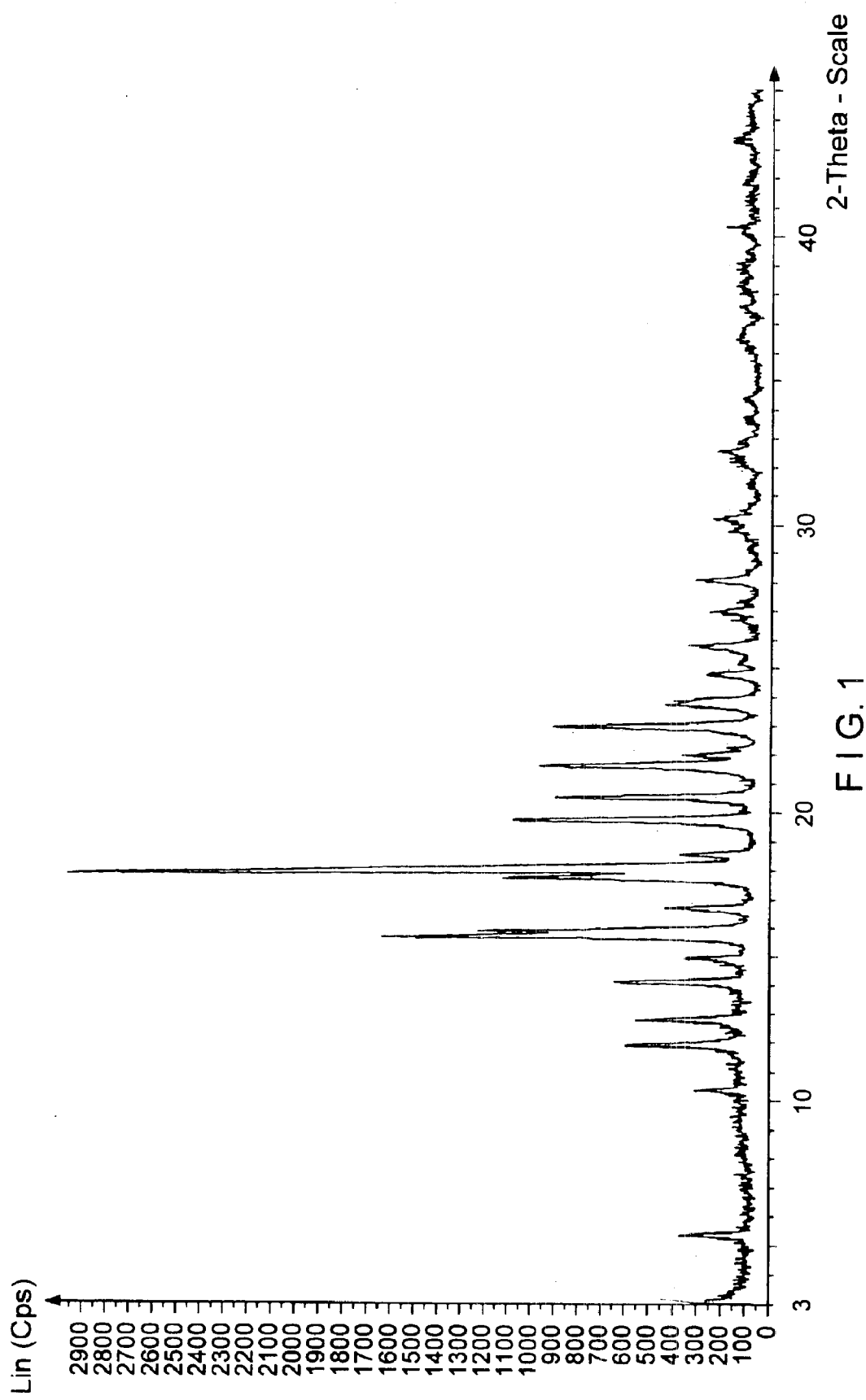
FIG. 1 shows an X-Ray powder diffractogram of crystalline Form I of dutasteride.

The crystalline Form I of dutasteride obtained in the above process is characterized by the X-ray powder diffraction pattern with d-spacings (in ° A) of the identified peaks in the X-ray diffractogram are 16.85, 8.59, 7.44, 6.93, 6.29, 5.95, 5.63, 5.58, 5.32, 4.98, 4.89, 4.78, 4.49, 4.32, 4.10, 4.04, 3.86, 3.75, 3.59, 3.46, 3.30, 3.17, 2.95, 2.75, 2.65, 2.39 and 2.23. The preferred crystalline Form I of dutasteride has substantially the same X-ray diffraction pattern as shown in FIG. 1.

In another embodiment, the invention also provides a process for the preparation of crystalline Form II of dutasteride that includes:
(i) dissolving the crude dutasteride in alcoholic solvents having $C_1-C_5$ carbon atoms, preferably methanol;
(ii) distilling the solvent from the reaction solution;

(iii) adding ester solvents such as ethyl acetates to the resultant residue obtained in step (ii);
(iv) filtering the crystallized solid accompanied by drying the compound in conventional methods to afford the novel crystalline Form II of dutasteride.

Figure 2:
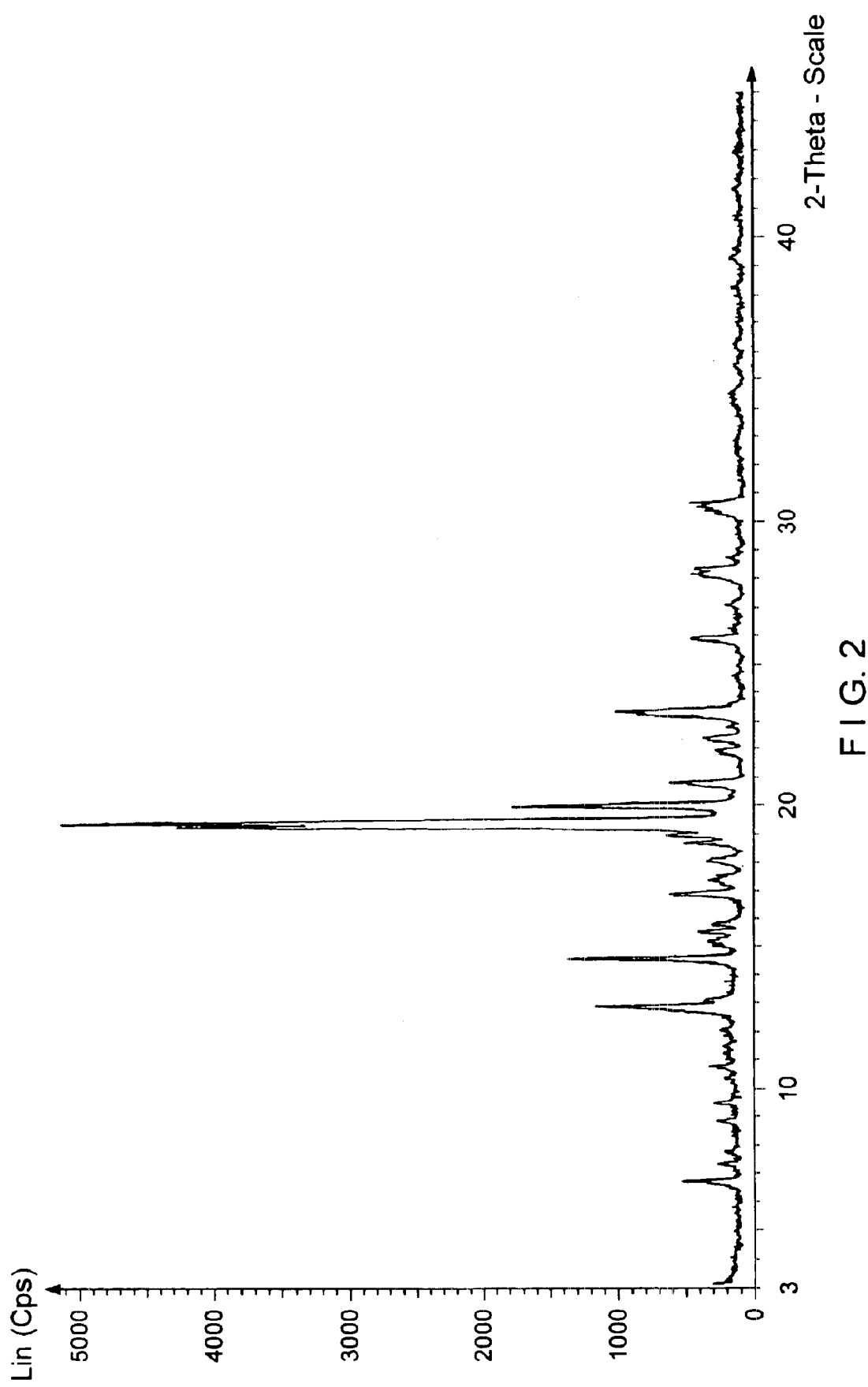
FIG. 2 shows an X-Ray powder diffractogram of crystalline Form II of dutasteride.
Figure 3:
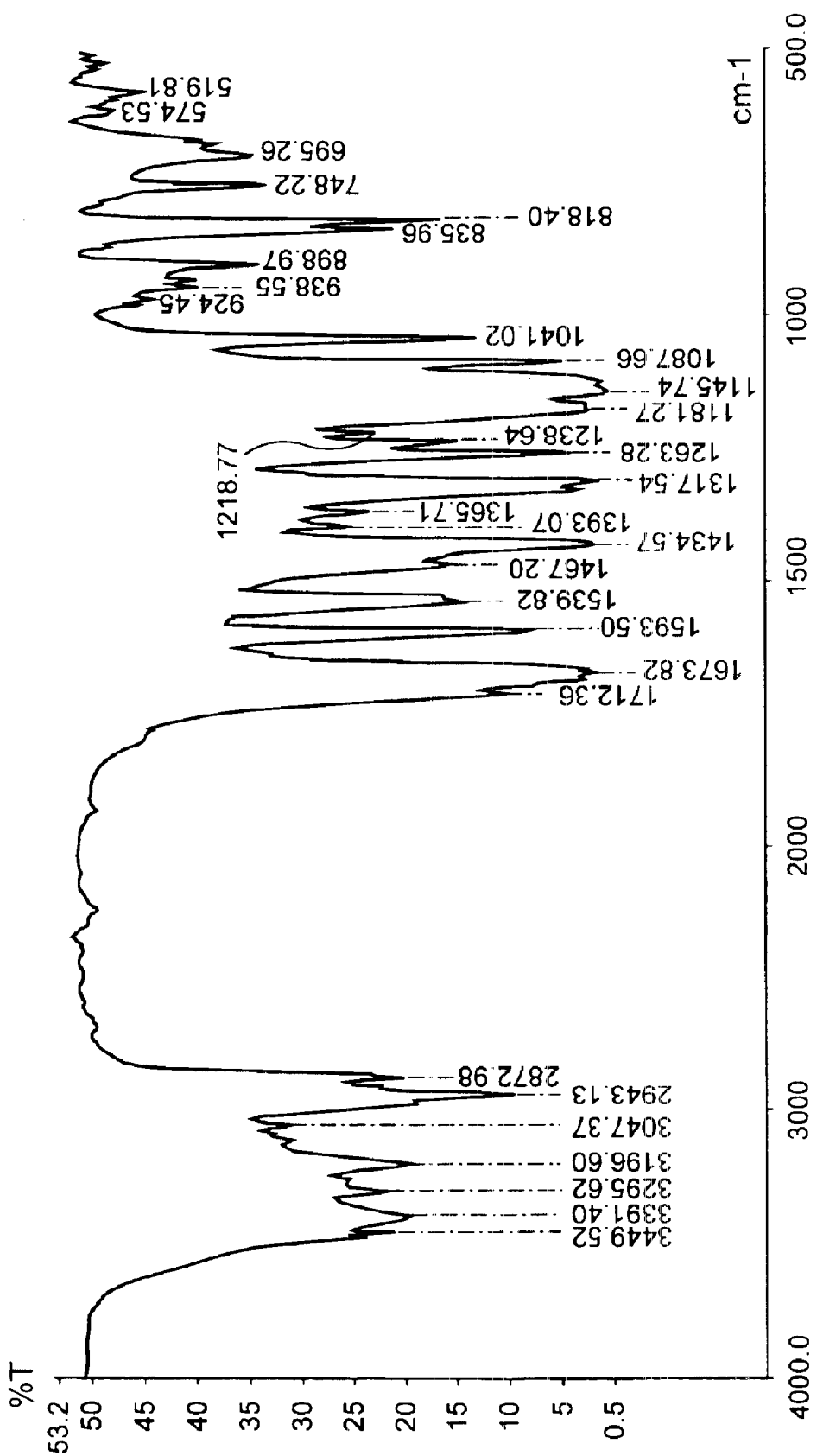
FIG. 3 shows an infrared spectrum of crystalline Form II of dutasteride.

The crystalline Form II of dutasteride obtained in the above process is characterized by the X-ray powder diffraction pattern in which d-spacings (in ° A) of the identified peaks in the X-ray diffractogram are 13.42, 12.25, 10.18, 9.43, 8.64, 8.34, 7.98, 7.41, 6.96, 6.80, 6.13, 5.93, 5.84, 5.27, 5.12, 4.93, 4.77, 4.70, 4.58, 4.46, 4.29, 4.08, 3.99, 3.91, 3.82, 3.63, 3.45, 3.29, 3.18, 3.12, 2.94, 2.35, and 2.30. The preferred crystalline Form II of dutasteride has substantially the same X-ray diffraction pattern as shown in FIG. 2. The infrared spectrum of the crystalline Form II of dutasteride includes peaks at about 818.56, 835.98, 1041.23, 1087.77, 1218.92, 1238.97, 1263.35, 1317.75, 1365.64, 1434.43, 1593.48, 1673.62, 2873.06, 2943.03, 3197.02, 3295.55, 3391.29, and 3449.55 $cm^{-1}$. The preferred crystalline Form II of dutasteride has substantially the same infrared spectrum as shown in FIG. 3.

The present invention also provides an amorphous form of dutasteride and a process for its preparation. In one embodiment, a process for preparation of an amorphous form of dutasteride includes:
(v) dissolving a crude form of dutasteride in an alcoholic solvent having $C_1$–$C_5$ carbon atoms, preferably methanol;
(vi) distilling the solvent from the reaction solution completely;
(vii) scratching solid by using conventional methods to afford the novel amorphous form of dutasteride.

Figure 4:
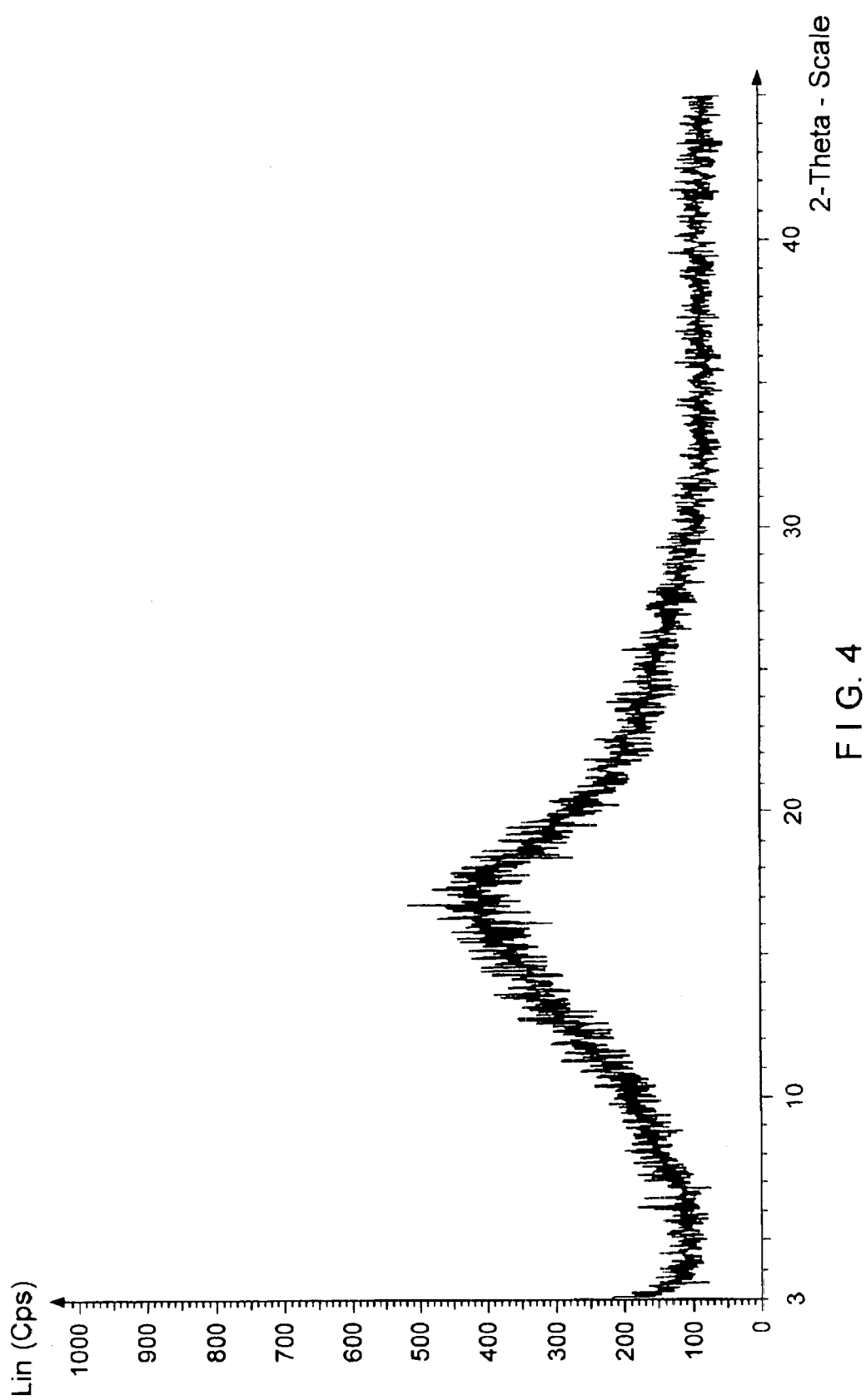
FIG. 4 shows an X-Ray powder diffractogram of an amorphous form of dutasteride.
Figure 5:
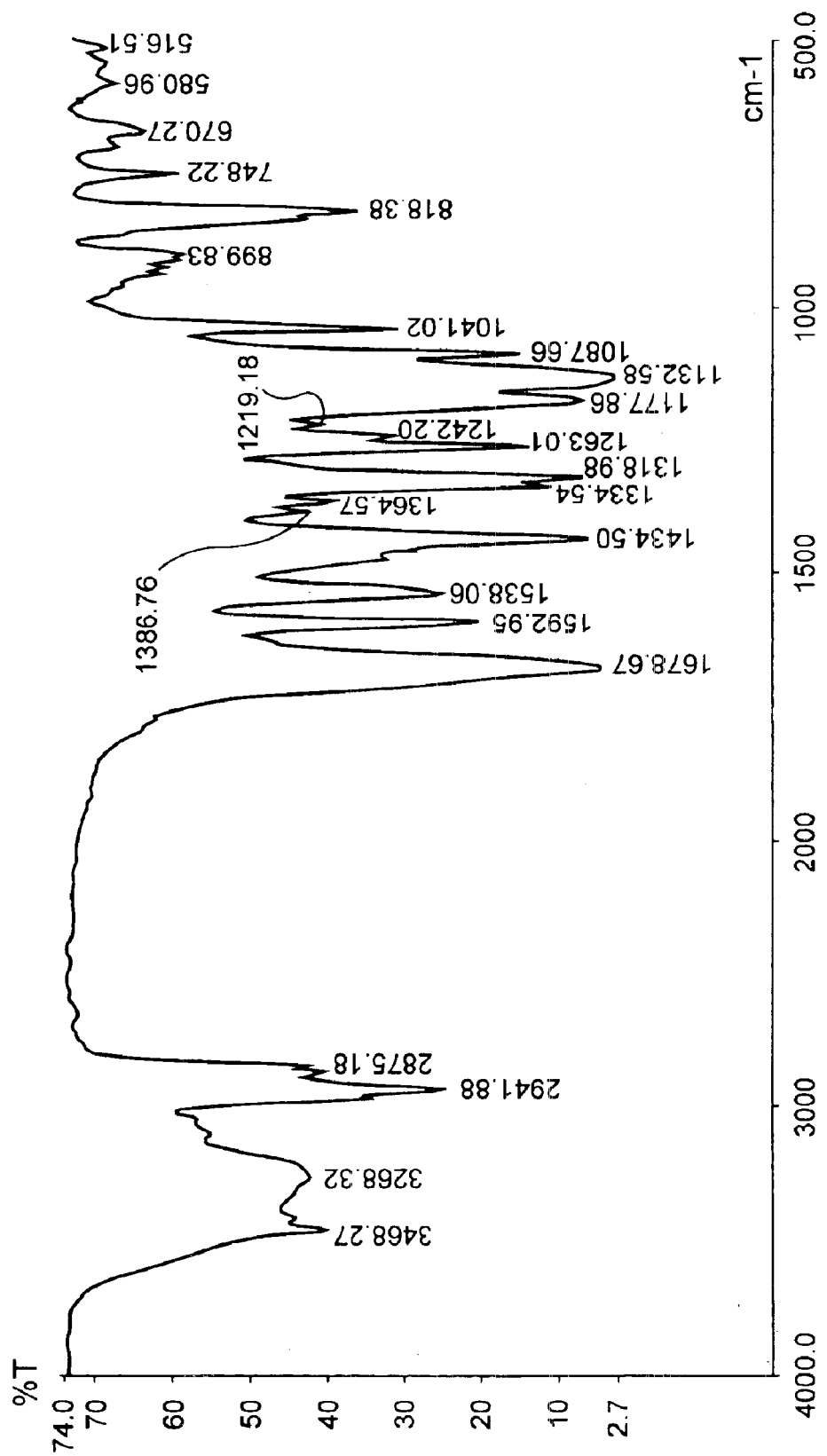
FIG. 5 shows an infrared spectrum of an amorphous form of dutasteride.

The amorphous form of dutasteride obtained by the above process is characterized by X-ray powder diffraction analysis and infrared spectrroscopy. The X-ray diffractogram shown in FIG. 4 is the preferred form of the amorphous dutasteride. It is obtained on Bruker Axe, DS Advance Powder X-ray Diffractometer with Cu K alpha-1 Radiation source. The infrared spectrum of the amorphous form of dutasteride includes absorption peaks at 818.38, 1041.03, 1087.33, 1132.58, 1177.86, 1219.18, 1242.20, 1263.01, 1318.98, 1334.54, 1364.57, 1386.76, 1434.50, 1538.06, 1592.95, 1678.67, 2875.18, 2941.88, 3268.32 and 3468.27 $cm^{-1}$.

The invention also provides formulations that include dutasteride as an active ingredient, together with a carrier and, optionally, other therapeutically active ingredients. The carrier must be pharmaceutically acceptable, that is being compatible with the other ingredients of the formulation and not deleterious to the recipient. The formulations include those suitable for oral, topical, rectal or parenteral (including subcutaneous, intramuscular and intravenous) administration. Preferred are those suitable for oral or parenteral administration. The formulations may in a unit dosage form and may be prepared by methods well known in the art of pharmacy. The preparation methods typically include the step of bringing the active compound into association with a carrier, which constitutes one or more accessory ingredients. In general, the formulations are prepared by uniformly and intimately bringing the active compound into association with a liquid carrier or a finely divided solid carrier and then, if necessary, shaping the product into desired unit dosage form. Formulations suitable for oral administration may be discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier. A syrup or suspension may be made by adding the active compound to a concentrated, aqueous solution of a sugar, e.g., sucrose, to which may also be added any additional ingredients. Such additional ingredient(s) may include flavorants, retardants, diluents, buffers, flavoring agents, binders, surface active agents, thickeners, lubricants, suspending agents, preservatives (including antioxidants) and the like. Formulations suitable for parenteral administration may be in a form of a sterile aqueous preparation of dutasteride; preferably, isotonic with the blood of the recipient. Such formulations may conveniently contain distilled water, dextrose in distilled water or saline and dutasteride. Topical formulations include ointments, creams, gels and lotions, which may be prepared by conventional methods. In addition to the ointment, cream gel, or lotion base and the active ingredient, such topical formulation may also contain preservatives, perfumes, and additional active pharmaceutical agents.

The invention will be explained in more detail with reference to the following examples, which are provided by way of illustration only and should not be constructed as limit to the scope of the reaction in any manner.

EXAMPLE 1

Preparation of Amorphous form of Dutasteride 10 grams of crude dutasteride (prepared as per the prior art methods) were dissolved in 60 ml of methanol with stirring. The reaction solution was filtered and washed with 20 ml of methanol. The solvent was distilled off completely under reduced pressure. The separated solid was scratched to provide the desired amorphous form of dutasteride (9.8 grams, 98% of yield).

EXAMPLE 2

Preparation of Crystalline Form I of Dutasteride 5.0 grams of crude dutasteride (prepared as per the prior art methods) were dissolved in 25 ml of dichloromethane with stirring. The solvent was partially distilled off (about 80%) under reduced pressure. 50 ml of cyclohexane was added to the resulting residue and the mixture was stirred at 50–60° C. for about 45 minutes. The separated solid was filtered at 50–60° C., and washed with 10 ml of cyclohexane. The obtained solid was dried at 80–90° C. for 3 hours to get the desired crystalline Form I of dutasteride (4.5 grams, 90% of yield).

EXAMPLE 3

Preparation of Crystalline Form II of Dutasteride 30.0 grams of crude dutasteride (prepared as per the prior art methods) and 210 ml of methanol were charged into a 1L liter round-bottomed flask. The solvent was heated to reflux until a clear solution was obtained. 3 grams of charcoal were added, and the solution was stirred at the same temperature for about 15 minutes. The contents were filtered through hi-flow bed and washed with 30 ml of methanol. The filtrate was concentrated under reduced pressure and 30 ml of ethyl acetate were added, followed by complete distillation off of solvents under reduced pressure. Charged 90 ml of ethyl acetate to the residue and stirred at 60–65° C. Cooled the reaction solution to 25–35° C. and stirred at the temperature for 45 minutes. Filtered the separated solid and washed with 30 ml of ethyl acetate. Dried the obtained solid at 70–80° C. up to get the constant weight of the desired crystalline Form-II of dutasteride (22 grams, 73.3% of yield).

Unless stated to the contrary, any use of the words such as "including," "containing," "comprising," "having" and the like, means "including without limitation" and shall not be construed to limit any general statement that it follows to the specific or similar items or matters immediately following it. Except where the context indicates to the contrary, all exemplary values are intended to be fictitious, unrelated to actual entities and are used for purposes of illustration only. Most of the foregoing alternative embodiments are not mutually exclusive, but may be implemented in various combinations. As these and other variations and combinations of the features discussed above can be utilized without departing from the invention as defined by the claims, the foregoing description of the embodiments should be taken by way of illustration rather than by way of limitation of the invention as defined by the appended claims.

What is claimed is:

1. A crystalline Form II of 17β-N-[2,5-bis (trifluoromethyl) phenyl]carbamoyl-4-aza-5α-androst-1-en-3-one (dutasteride).

2. The crystalline form of dutasteride of claim 1 having an X-ray powder diffraction pattern expressed in terms of d-spacing (in ° A), said diffraction pattern includes peaks at about 13.42, 6.96, 6.13, 5.27, 4.77, 4.70, 4.58, 4.46 and 3.82.

3. The crystalline form of dutasteride of claim 1, wherein the X-ray powder diffraction pattern substantially the same shown in FIG. 2.

4. The crystalline form of dutasteride of claim 1 having an infrared spectrum that includes peaks at about 818.56, 835.98, 1041.23, 1087.77, 1218.92, 1238.97, 1263.35, 1317.75, 1365.64, 1434.43, 1593.48, 1673.62, 2873.06, 2943.03, 3197.02, 3295.55, 3391.29, and 3449.55 cm$^{-1}$.

5. A process for preparation of a crystalline Form II of dutasteride, said process comprising:
   (i) dissolving a crude form of dutasteride in an alcoholic solvent having from 1 to 5 carbon atoms;
   (ii) removing said alcoholic solvent thereby obtaining a residue;
   (iii) adding an ester solvent to said residue thereby obtaining a separated solid; and
   (iv) filtering the separated solid that is said crystalline Form II of dutasteride.

6. The process of claim 5, wherein said alcoholic solvent is methanol.

7. The process of claim 5, wherein said ester solvent is ethyl acetate.

8. The process of claim 5, further comprising drying said separated solid.

9. A process for the preparation crystalline Form I of dutasteride, said process comprising:
   (i) dissolving a crude dutasteride in a halogenated hydrocarbon solvent;
   (ii) removing said solvent thereby obtaining a residue;
   (iii) adding an aliphatic hydrocarbon solvent of low molecular to said residue thereby obtaining a separated solid; and
   (iv) filtering the separated solid that is said crystalline Form I of dutasteride.

10. The process of claim 9, further comprising drying said separated solid.

11. The process of claim 9, wherein said halogenated solvent is dichloromethane.

12. The process of claim 9, wherein said aliphatic solvent is cyclohexane.

13. An amorphous form of 17β-N-[2,5-bis (trifluoromethyl) phenyl]carbamoyl-4aza-5-α-androst-1-en-3-one (dutasteride).

14. The amorphous form of dutasteride of claim 1 having an X-ray powder diffraction substantially the same as shown in FIG. 4.

15. A process for preparation of novel amorphous form of dutasteride, said process comprising:
   i) dissolving a crude form of dutasteride in an alcoholic solvent having from 1 to 5 carbon atoms;
   ii) removing said alcoholic solvent to obtain a solid residue;
   iii) isolating said solid residue to afford the amorphous form of dutasteride.

16. The process of claim 15, wherein said alcoholic solvent is methanol.

* * * * *

UNITED STATES PATENT AND TRADEMARK OFFICE
CERTIFICATE OF CORRECTION

PATENT NO. : 7,022,854 B2
APPLICATION NO. : 10/622098
DATED : April 4, 2006
INVENTOR(S) : Manne Satyanarayana Reddy et al.

It is certified that error appears in the above-identified patent and that said Letters Patent is hereby corrected as shown below:

On the Title page, add the following under the heading item (30) Foreign Application Priority Data:

June 23, 2003    (IN)    523/MAS/2003

Signed and Sealed this

Third Day of October, 2006

JON W. DUDAS
*Director of the United States Patent and Trademark Office*